US012661357B2

(12) United States Patent
Li et al.

(10) Patent No.: US 12,661,357 B2
(45) Date of Patent: Jun. 23, 2026

(54) USE OF PYRIDO[1,2-A]PYRIMIDONE ANALOGUE

(71) Applicants: GUANGZHOU JOYO PHARMATECH CO., LTD, Guangdong (CN); SHANGHAI JIA TAN PHARMATECH CO., LTD., Shanghai (CN)

(72) Inventors: Yongguo Li, Shanghai (CN); Wei Wei, Shanghai (CN); Wei Ye, Shanghai (CN)

(73) Assignees: GUANGZHOU JOYO PHARMATECH CO., LTD, Guangdong (CN); SHANGHAI JIA TAN PHARMATECH CO., LTD., Shanghai (CN)

( * ) Notice: Subject to any disclaimer, the term of this patent is extended or adjusted under 35 U.S.C. 154(b) by 399 days.

(21) Appl. No.: 18/261,832

(22) PCT Filed: Jan. 24, 2022

(86) PCT No.: PCT/CN2022/073567
§ 371 (c)(1),
(2) Date: Jul. 17, 2023

(87) PCT Pub. No.: WO2022/156803
PCT Pub. Date: Jul. 28, 2022

(65) Prior Publication Data

US 2024/0091229 A1 Mar. 21, 2024

(30) Foreign Application Priority Data

Jan. 25, 2021 (CN) ......................... 202110095016.5

(51) Int. Cl.

| | |
|---|---|
| *A61K 31/519* | (2006.01) |
| *A61K 9/00* | (2006.01) |
| *A61P 35/00* | (2006.01) |
| *C12Q 1/6886* | (2018.01) |
| *C07D 471/04* | (2006.01) |

(52) U.S. Cl.
CPC .......... *A61K 31/519* (2013.01); *A61K 9/0053* (2013.01); *A61P 35/00* (2018.01); *C12Q 1/6886* (2013.01); *C12Q 2600/156* (2013.01)

(58) Field of Classification Search
None
See application file for complete search history.

(56) References Cited

U.S. PATENT DOCUMENTS 9,868,737 B2 * 1/2018 Guan ................... C07D 487/04
2016/0137634 A1 * 5/2016 Barlaam ................. A61P 43/00 544/405
2023/0165864 A1 6/2023 Li et al.

FOREIGN PATENT DOCUMENTS

CN 105461712 A 4/2016
CN 114796228 A 7/2022
WO 2015192761 A1 12/2015
WO WO-2017101829 A1 * 6/2017 ........... C07D 471/04
WO 2021219101 A1 11/2021
WO 2022152296 A1 7/2022

OTHER PUBLICATIONS

WO2017101829a1, English Translation (Year: 2017).*
Janku et al., Targeting the PI3K pathway in cancer: are we making headway?, Nat Rev Clin Oncol 15, 273-291 (2018) (Year: 2018).*
Shi et al., Inhibition of esophageal cancer growth through thesuppression of PI3K/AKT/mTOR signaling pathway, Onco Targets and Therapy 2019:12 7637-7647 (Year: 2019).*
Vasconcelos et al., Immunoprofile of c-MET/PI3K signaling in human salivary gland tumors. vol. 120 No. 2 Aug. 2015 (Year: 2015).*
Esmaeli et al., RAS Mutations Coexist with PIK3CA and MET Mutations in Lacrimal Gland Epithelial Neoplasms. ARVO Annual Meeting Abstract | Jun. 2013 (Year: 2013).*
Wang et al., Profiling of 149 Salivary Duct Carcinomas, Carcinoma Ex Pleomorphic Adenomas, and Adenocarcinomas, Not Otherwise Specified Reveals Actionable Genomic Alterations, Clin Cancer Res; 22(24) Dec. 15, 2016 (Year: 2016).*
Yu et al., PI3K-PKB-mTOR hyperactivation in relation tonasopharyngeal carcinoma progression and prognosis, J Cell Biochem. 2019;120:10186-10194 (Year: 2019).*
Apr. 24, 2022 International Search Report issued in International Patent Application No. PCT/CN2022/073567.

(Continued)

*Primary Examiner* — Kortney L. Klinkel
*Assistant Examiner* — Alison Azar Hastings
(74) *Attorney, Agent, or Firm* — Houston Beshining Law Office PLLC; Liangang Ye

(57) ABSTRACT

Use of a pyrido[1,2-a]pyrimidone analogue. Specifically disclosed is use of a compound I or a pharmaceutically acceptable salt thereof in the preparation of a medicament for treating and/or preventing cancers in the digestive tract system. The compound I or the pharmaceutically acceptable salt thereof has good antitumor activity against one or more of head and neck cancer, hepatocellular cancer, colorectal cancer, esophageal cancer, gastric cancer and nasopharyngeal cancer.

I

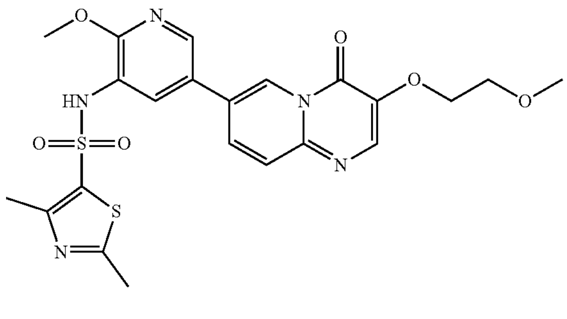

14 Claims, 1 Drawing Sheet

(56) References Cited

OTHER PUBLICATIONS

Apr. 24, 2022 Written Opinion of the International Searching Authority issued in International Patent Application No. PCT/CN2022/073567.
Feb. 24, 2023 Chinese First Office Action issued in Chinese Patent Application No. 2022100282430.
Oct. 3, 2022 First Office Action issued in Taiwan Patent Application No. 111102822.
Mar. 14, 2023 Rejection Decision issued in Taiwan Patent Application No. 111102822.
Berge et al., "Pharmaceutical Salts", Journal of Pharmaceutical Science 66: 1-19 (1977).
Handbook of Pharmaceutical Salts: Properties, Selection, and Use (P. Heinrich Stahl and Camille G. Wermuth, ed., Wiley-VCH, 2002).
Handbook of Pharmaceutical Excipients (Raymond C Rowe, 2009 Sixth Edition).
Feb. 23, 2023 search report issued in Chinese Patent Application No. 2022100282430.

* cited by examiner

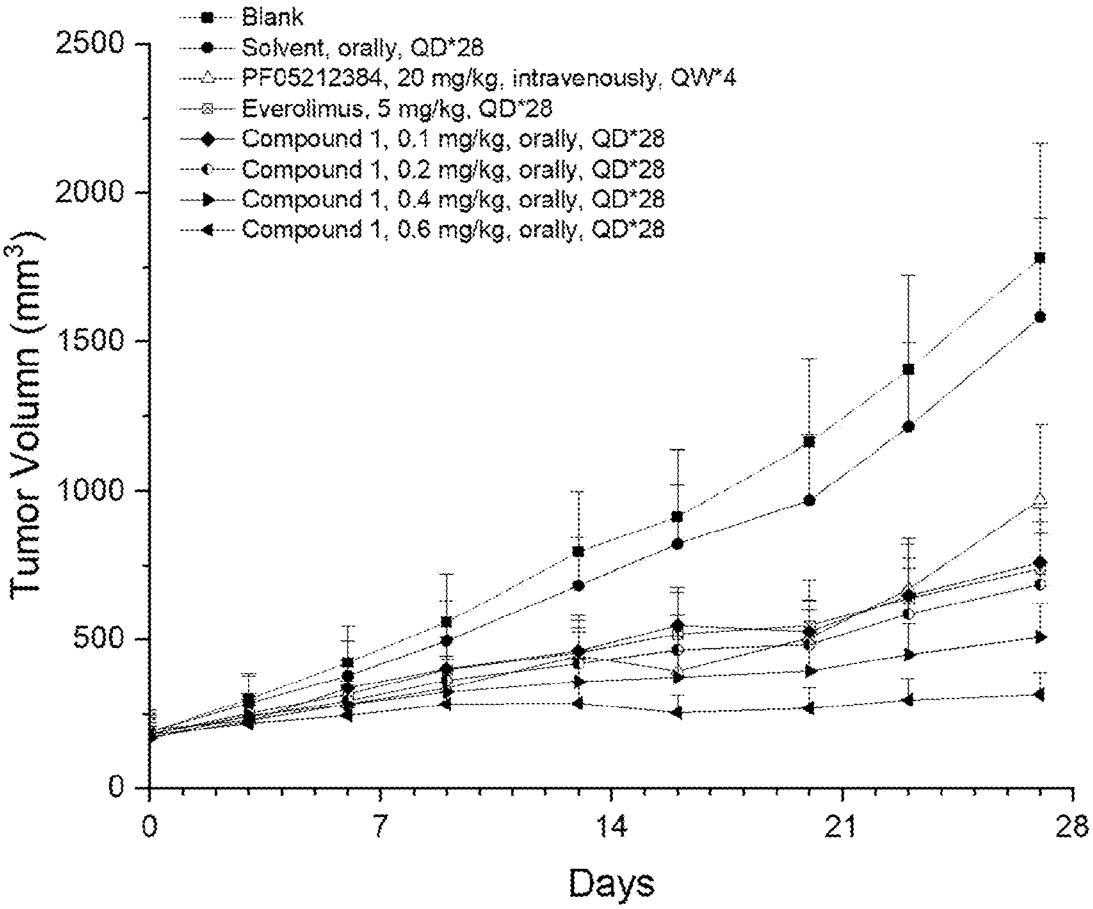
Blank
Solvent, orally, QD*28
PF05212384, 20 mg/kg, intravenously, QW*4
Everolimus, 5 mg/kg, QD*28
Compound 1, 0.1 mg/kg, orally, QD*28
Compound 1, 0.2 mg/kg, orally, QD*28
Compound 1, 0.4 mg/kg, orally, QD*28
Compound 1, 0.6 mg/kg, orally, QD*28
Tumor Volumn (mm3)
2500
2000
1500
1000
500
0
0
7
14
21
28
Days

USE OF PYRIDO[1,2-A]PYRIMIDONE ANALOGUE

The present application is a National Stage of International Application No. PCT/CN2022/073567, filed on Jan. 24, 2022, which claims priority of the Chinese Patent Application No. CN2021100950165 filed on Jan. 25, 2021, the content of which is incorporated herein by reference in its entirety.

TECHNICAL FIELD

The present disclosure relates to the technical field of biomedicine, in particular, the present disclosure relates to the use of pyrido[1,2-a]pyrimidinone analogue.

BACKGROUND

Malignant tumors are a type of disease that seriously threatens human life and health at present, whose morbidity and mortality are increasing year by year. Human mortality due to cancer ranks second only to cardiovascular and cerebrovascular diseases. The essence of carcinogenesis is that the molecular signals that regulate the physiological functions of cells are abnormal in the transduction process, which leads to the disorder of normal physiological functions of cells and infinite proliferation. Cell signal transduction is closely related to tumor occurrence, development, recurrence and metastasis. Traditional cytotoxic drugs for tumor treatment generally have disadvantages such as low selectivity, strong side effects and poor drug resistance, which promotes the transfer of the research direction of anti-tumor drugs to small molecule targeting drugs.

According to *Cancer Statistics in China,* 2015, there were about 4.3 million new cancer cases in China in 2015, and 2.8 million patients with cancers died. In recent years, with the development of anti-tumor drugs, the treatment effect of patients with advanced cancers has been greatly improved, but there are still many patients who do not respond to the existing treatments, or have poor efficacy, or develop drug resistance after treatment, which seriously affect their quality of life and threaten their lives. Therefore, it is still necessary to develop new anti-tumor drugs to benefit more patients.

PI3K-AKT-mTOR is an important pathway of cell cycle regulation, which is crucial to cell growth, division, survival and reproduction. Its transitional activation is involved in the occurrence, development, survival and migration of various tumors. PI3K (phosphatidylinositol 3-kinase), AKT and mTOR (mammalian target of rapamycin) are the key molecules of this pathway, so they become the targets of anti-tumor therapy. PI3K-specific or mTOR-specific inhibitors are already on the market, and the dual inhibitors of these two molecules can theoretically have better anti-tumor efficacy.

PF-05212384 (PKI-587) is a PI3K and mTOR dual-target inhibitor developed by Pfizer, which is currently in Phase II clinical trials. Everolimus is an oral mTOR single-target inhibitor developed by Novartis, with a trade name of Afinitor, which was approved for marketing by the FDA in March 2009. Internationally, Everolimus is approved for multiple indications: advanced renal cell carcinoma (RCC), tuberous sclerosis-associated subependymal giant cell astrocytoma (TSC-SEGA) and renal angiomyolipoma (TSC-AML), advanced pancreatic neuroendocrine tumors (pNET), postmenopausal estrogen receptor positive/HER-2 negative advanced breast cancer (BC) and other tumors.

CONTENT OF THE PRESENT INVENTION

The present disclosure provides a new use of pyrido[1,2-a]pyrimidinone analogue. This class of compound or pharmaceutically acceptable salt thereof has good antitumor activity on cancers in the digestive tract system, such as one or more than one of head and neck cancer, hepatocellular cancer, colorectal cancer, esophageal cancer, gastric cancer and nasopharyngeal cancer.

The present disclosure provides a use of compound I or a pharmaceutically acceptable salt thereof in the preparation of a medicament, the structure of the compound I is as follows:

I

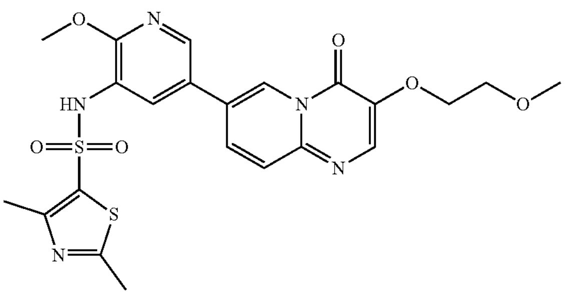

the medicament is used for treating and/or preventing cancers in the digestive tract system.

Herein, the cancer in the digestive tract system can be wild-type or PIK3CA-mutated cancer in the digestive tract system.

The cancer in the digestive tract system can be head and neck cancer. Preferably, the head and neck cancer can be PIK3CA wild-type head and neck cancer or PIK3CA-mutated head and neck cancer.

Preferably, the head and neck cancer can be pleomorphic adenoma, for example, malignant pleomorphic adenoma, further for example, right submandibular malignant pleomorphic adenoma.

Preferably, the head and neck cancer can be maxillary sinus carcinoma.

Preferably, the head and neck cancer can be adenoid cystic carcinoma.

The cancer in the digestive tract system can be hepatocellular cancer.

The cancer in the digestive tract system can be colorectal cancer.

The cancer in the digestive tract system can be esophageal cancer.

The cancer in the digestive tract system can be gastric cancer.

The cancer in the digestive tract system can be nasopharyngeal carcinoma.

In the present disclosure, the medicament is presented in an oral dosage form.

In the present disclosure, the medicament is presented in a tablet form.

The present disclosure further provides the compound I or the pharmaceutically acceptable salt thereof for use in treating and/or preventing cancers in the digestive tract system, the structure of the compound I is as follows:

I

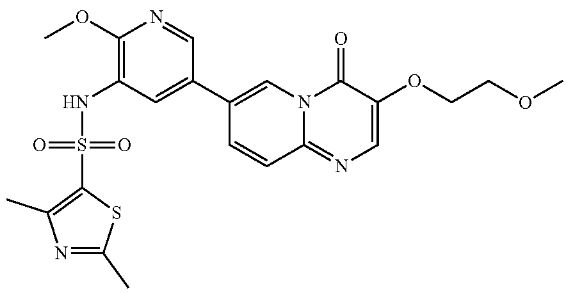

wherein the cancer in the digestive tract system is as described in any of the above embodiments.

The present disclosure provides a method for treating and/or preventing cancers in the digestive tract system, comprising administering to a patient a therapeutically effective amount of the compound I or the pharmaceutically acceptable salt thereof. The cancer in the digestive tract system is as described in any of the above embodiments.

In the use of the compound I or the pharmaceutically acceptable salt thereof in the preparation of the medicament or the method for treating and/or preventing cancers in the digestive tract system, the dosage of the compound I or the pharmaceutically acceptable salt thereof can be administered according to the weight of the subject/patient. Preferably, the administration dosage of the compound I or the pharmaceutically acceptable salt thereof is 0.1-2.0 mg/time, for example: 0.1 mg/time, 0.2 mg/time, 0.3 mg/time, 0.4 mg/time, 0.5 mg/time, 0.6 mg/time, 0.7 mg/time, 0.8 mg/time, 0.9 mg/time, 1.0 mg/time, 1.1 mg/time, 1.2 mg/time, 1.3 mg/time, 1.4 mg/time, 1.5 mg/time, 1.6 mg/time, 1.7 mg/time, 1.8 mg/time, 1.9 mg/time or 2.0 mg/time.

In the use or the method for treating and/or preventing cancers in the digestive tract system, the administration frequency of the compound I or the pharmaceutically acceptable salt thereof can be once a day or twice a day.

In the use or the method for treating and/or preventing cancers in the digestive tract system, the compound I or the pharmaceutically acceptable salt thereof can be administered orally.

Preferably, in the use or the method for treating and/or preventing cancer, the compound I or the pharmaceutically acceptable salt thereof is administered orally, and the administration dosage is 0.1-2.0 mg/time, for example, 0.1 mg/time, 0.4 mg/time, 0.5 mg/time, 0.6 mg/time, 0.7 mg/time, 0.9 mg/time or 1.1 mg/time, and the administration frequency is once a day.

In the use or the method for treating and/or preventing cancers in the digestive tract system, it can further include the step of detecting whether the patient carries PIK3CA gene mutation.

The present disclosure also provides a combined kit, comprising kit A and kit B;

wherein the kit A comprises reagents for detecting PIK3CA gene mutation; the kit B comprises the compound I or the pharmaceutically acceptable salt thereof.

Preferably, the administration time of the kit A and the kit B are in no particular order, or the kit A is administered first between the kits.

Preferably, in the kit A, the reagent for detecting PIK3CA gene mutation is used for detecting whether a patient with cancers in the digestive tract system (such as head and neck cancer) carries PIK3CA gene mutation.

Preferably, in the kit B, the amount of the compound I or the pharmaceutically acceptable salt thereof is a therapeutically effective amount.

Preferably, the kit B also comprises pharmaceutically acceptable excipients.

Preferably, in the kit B, the dosage and administration frequency of the compound I or the pharmaceutically acceptable salt thereof are as described in any of the above embodiments.

Preferably, the combined kit is used for treating and/or preventing cancers in the digestive tract system, and the cancer in the digestive tract system is as described in any of the above embodiments.

Unless otherwise specified, the following terms and phrases used herein are intended to have the following meanings. A specific term or phrase should not be considered indefinite or unclear if it is not specifically defined, but should be understood according to its ordinary meaning. When a trade name appears herein, it is intended to refer to its corresponding trade name or its active ingredient.

The term "pharmaceutically acceptable" as used herein refers to those compounds, materials, compositions and/or dosage forms, which are suitable for use in contact with human and animal tissues within the scope of sound medical judgment, without undue toxicity, irritation, allergic reaction or other problems or complications, commensurate with a reasonable benefit/risk ratio.

The term "pharmaceutically acceptable salt" refers to a salt prepared from the compound of the present disclosure with a relatively non-toxic, pharmaceutically acceptable acid or base. When the compound of the present disclosure contains relatively acidic functional groups, the base addition salt can be obtained by contacting the neutral form of such compound with a sufficient amount of a pharmaceutically acceptable base in pure solution or in a suitable inert solvent. Pharmaceutically acceptable base addition salts include but are not limited to lithium salts, sodium salts, potassium salts, calcium salts, aluminum salts, magnesium salts, zinc salts, bismuth salts, ammonium salts, diethanolamine salts. When the compound of the present disclosure contains relatively basic functional groups, the acid addition salt can be obtained by contacting the neutral form of such compound with a sufficient amount of a pharmaceutically acceptable acid in pure solution or in a suitable inert solvent. The pharmaceutically acceptable acid includes inorganic acids. The inorganic acids include but not limited to hydrochloric acid, hydrobromic acid, hydroiodic acid, nitric acid, carbonic acid, phosphoric acid, phosphorous acid, sulfuric acid and the like. The pharmaceutically acceptable acids include organic acids. The organic acids include but not limited to acetic acid, propionic acid, oxalic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, salicylic acid, tartaric acid, methanesulfonic acid, isonicotinic acid, acid citric acid, oleic acid, tannic acid, pantothenic acid, bitartaric acid, ascorbic acid, gentisic acid, fumaric acid, gluconic acid, sugar acid, formic acid, ethanesulfonic acid, pamoic acid (i.e., 4,4'-methylene-bis(3-hydroxy-2-naphthoic acid), amino acids (such as glutamic acid, arginine), etc. When the compound of the present disclosure contains relatively acidic and relatively basic functional groups, it can be converted into base addition salts or acid addition salts. For details, see Berge et al., "Pharmaceutical Salts", Journal of Pharmaceutical Science 66: 1-19 (1977), or, Handbook of Pharmaceutical Salts: Properties, Selection, and Use (P. Heinrich Stahl and Camille G. Wermuth, ed., Wiley-VCH, 2002).

The term “treatment” refers to therapeutic therapy. In relation to a specific condition, treatment means: (1) one or more biological manifestations of amelioration of the disease or condition, (2) interference with (a) one or more points in the biological cascade leading to or causing the condition or (b) one or more biological manifestations of the condition, (3) amelioration of one or more symptoms, effects or side effects associated with the condition, or one or more symptoms, effects or side effects associated with the condition or the treatment thereof, or (4) amelioration of the condition or the development of one or more biological manifestations of the condition.

The term “prevent” refers to a reduction in the risk of contracting or developing a disease or disorder.

The term “therapeutically effective amount” refers to an amount of a compound sufficient to effectively treat a disease or condition described herein when administered to a patient. A “therapeutically effective amount” will vary depending on the compound, the condition and the severity thereof, and the age of the patient to be treated, but it can be adjusted as necessary by those skilled in the art.

The term “pharmaceutically acceptable excipients” refers to the excipients and additives used in the production of medicaments and formulation of prescriptions, and refers to all substances contained in the pharmaceutical formulation except active ingredients. See Pharmacopoeia of the People’s Republic of China (2020 Edition) Volume Four or Handbook of Pharmaceutical Excipients (Raymond C Rowe, 2009 Sixth Edition).

The term “patient” refers to any animal, preferably a mammal, and most preferably a human, that is about to or has received the administration of the compound according to the examples of the present disclosure. The term “mammal” includes any mammal. Examples of mammals include but are not limited to cows, horses, sheep, pigs, cats, dogs, mice, rats, rabbits, guinea pigs, monkeys, humans, etc., most preferably a human.

On the basis of not violating common knowledge in the art, the above-mentioned preferred conditions can be combined arbitrarily to obtain preferred examples of the present disclosure.

The reagents and raw materials used in the present disclosure are all commercially available.

The positive and progressive progress effect of the present disclosure is that compound I has good antitumor activity against one or more than one of head and neck cancer, hepatocellular cancer, colorectal cancer, esophageal cancer, gastric cancer and nasopharyngeal cancer.

BRIEF DESCRIPTION OF THE DRAWINGS

FIG. 1 is the in vivo drug efficacy result of compound I on human-derived colorectal cancer CO-04-0032 subcutaneous xenograft tumor model in nude mice.

DETAILED DESCRIPTION OF THE PREFERRED EMBODIMENT

The present disclosure is further illustrated below by means of examples, but the present disclosure is not limited to the scope of the examples. The experimental methods that haven’t illustrated specific conditions in the following examples are selected according to conventional methods and conditions, or according to the product instructions.

Compound I in the following examples refers to

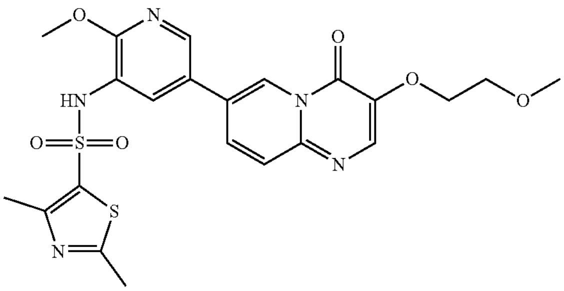

, which is a pyrido[1,2-a]pyrimidinone analogue.

Example 1 the $IC_{50}$ of Compound I on Head and Neck Cancer and/or Hepatocellular Cancer Cell Lines was Determined by CTG Method 1. Experimental Materials (1) Cell Lines

TABLE 1

Head and neck cancer and/or hepatocellular cancer cell lines

| Cell name | Organization type | Cultural characteristics | Culture medium | Cells seeded per well |
|---|---|---|---|---|
| RPMI 2650 | Head/neck | Adherent | (MEM + 0.01 mM NEAA) + 10% FBS | 4000 |
| CAL-27 | Head/neck | Adherent | DMEM + 10% FBS | 2000 |
| Hep G2 | Liver | Adherent | (MEM + 0.01 mM NEAA) + 10% FBS | 5000 |

TABLE 2

Esophageal cancer cell lines

| Cell name | Organization type | Cultural characteristics | Culture medium | Cells seeded per well |
|---|---|---|---|---|
| KYSE-150 | Esophageal cancer | Adherent | RPMI 1640/F12 medium + 10% FBS | 3000 |
| TE-1 | Esophageal cancer | Adherent | DMEM + 10% FBS | 3000 |

Note: 1).
Cell culture conditions were: 37° C., 5% $CO_2$ and 95% humidity.

2). $IC_{50}$ value: the concentration of inhibitor when 50% inhibitory effect was achieved;

3). CAL-27 and RPMI 2650: head and neck cancer cell models; HepG2: hepatocellular cancer cells. CAL-27, RPMI 2650 and HepG2 cells were purchased from ATCC, where ATCC® No. was CRL-2095™, CCL-30™, HB-8065™, respectively.

4). Both KYSE-150 and TE-1 were esophageal cancer cell models. The KYSE-150 cell line was purchased from DSMZ (German Collection of Microorganisms and Cell Cultures), and the DSMZ No. was ACC375; the TE-1 cell line was purchased from National Collection of Authenticated Cell Cultures, catalog number: TCHu89.

5). RPMI 1640/F12 medium was a 1:1 mixture of RPMI 1640 medium and F12 medium.

6). The percentages in 10% FBS in Table 1 and Table 2 were volume percentages.

(2) Reagents

1). FBS (fetal bovine serum) (purchased from ExCell, product number: FND500);

2). MEM medium (purchased from Hyclone, product number: SH30024.01;

3). DMEM medium (purchased from Gibco, product number: C11995500BT);

4). MEM NEAA (purchased from Gibco, product number: 11140-050);

5). RPMI1640 Culture medium (purchased from Gibco, product number: 11875-119);

6). F12 Culture medium (purchased from Gibco, product number: 11765-054);

(3) Test Article and Positive Control Article

Test article: compound I;

Positive control article: Cisplatin, molecular weight: 300.05; solvent: PBS (phosphate buffer saline); storage condition: 2-8° C.; supplier: Qilu Pharmaceutical.

Positive control article: Alpelisib, molecular weight: 441.47; solvent: DMSO; supplier: Shanghai TOPSCIENCE Biochemical Technology Co., Ltd., CAS number: 1217486-61-7;

2. CTG Method was Used to Determine the Cell Proliferation $IC_{50}$ of the Compound Step 1: Cells in exponential growth phase were harvested, and viable cells were counted with a Vi-Cell XR cytometer. The cell suspension was adjusted to an appropriate concentration with medium. 90 μL of cell suspension was added to each well of a 96-well cell culture plate, and the final cell concentration was 1500-6000 cells/well.

Step 2: The initial concentration of administration of compound I is 3 μM, and the initial concentration of administration of the control drug Alpelisib and Cisplatin was 10 μM, serially diluted 3-fold, a total of 9 concentration gradients and a DMSO control, the final concentration of DMSO in each well was 0.1%, placed in a 37° C., 5% $CO_2$ incubator for 72 hours.

Step 3: After 72 hours of drug treatment, 50 μL (½ culture volume) CTG solution that was melted and equilibrated to room temperature was added to each well according to the CTG operation instructions. The solution was mixed well with a microplate shaker for 2 minutes, and placed at room temperature. After 10 minutes, the fluorescence signal value was measured with an Envision2104 plate reader.

3. Data Analysis

Cell survival rate was calculated using the formula: $V_{sample}/V_{vehicle\ control}\times100\%$. Where, $V_{sample}$ was the reading of the drug treatment group, and $V_{vehicle\ control}$ was the average value of the solvent control group. GraphPad Prism 5.0 software was used, and a S-type dosage-survival rate curve was drawn using a nonlinear regression model and $IC_{50}$ value was calculated.

4. Experimental Results

TABLE 3

$IC_{50}$ values of compound I and Cisplatin on each tested cell line

| Cell name | Compound I Absolute $IC_{50}$ (μM) | Cisplatin Absolute $IC_{50}$ (μM) |
|---|---|---|
| RPMI2650 | 0.073 | 4.250 |
| CAL-27 | 0.073 | 4.371 |
| HepG2 | 0.574 | 11.124 |

In conclusion, it could be seen from the experimental results in Table 3 that the concentration of the inhibitor was lower than 1 μM when compound I achieved 50% inhibitory effect on RPMI2650, CAL-27 and HepG2 tumor cells.

TABLE 4

$IC_{50}$ values of compound I and Alpelisib on each tested cell line

| Cell name | Compound I Absolute $IC_{50}$ (μM) | Alpelisib Absolute $IC_{50}$ (μM) |
|---|---|---|
| KYSE-150 | 0.034 | 2.113 |
| TE-1 | 0.131 | >3 |

In conclusion, it could be seen from the experimental results in Table 4 that the concentration of the inhibitor was lower than 1 μM when compound I achieved 50% inhibitory effect on KYSE-150 and TE-1 tumor cells, which had a significant curative effect compared with that of the control positive compound Alpelisib (half inhibitory concentration >2 μM).

Example 2 Study on the In Vivo Pharmacodynamics of the Test Drug on the Human-Derived Colorectal Cancer CO-04-0032 Subcutaneous Xenograft Tumor Model in Nude Mice Experimental purpose: Study the in vivo efficacy of the test drug on human-derived colorectal cancer CO-04-0032 subcutaneous xenograft tumor model in nude mice.

Experimental design:

(1) Animals: BALB/c nude mice, female, 6 weeks old, weighing 16-18 grams. Provided by Shanghai Sippe-Bk Lab Animal Co., Ltd.

(2) Control article:

Both PF05212384 and Everolimus were purchased from Shanghai TOPSCIENCE Biochemical Technology Co., Ltd.

(3) Tumor inoculation: CO-04-0032 tumor mass with a volume of about 30 $mm^3$ was subcutaneously inoculated on the right back of each mouse, and the mice were divided into groups and administered with drugs when the average tumor volume reached 182 $mm^3$. CO-04-0032 was a PDX model of human-derived colon cancer independently developed by WuXi AppTec New Drug Development Co., Ltd. See Table 5 below for the experimental grouping and dosing regimen.

TABLE 5

| Group | Number of animals | Drug | Dose (mg/kg) | Administration volume (μL/g) | Route of administration | Administration frequency |
|---|---|---|---|---|---|---|
| 1 | 8 | Blank | — | — | — | — |
| 2 | 8 | Solvent | — | 10 | Oral | Once a day for 28 days |
| 3 | 8 | PF05212384 | 20 | 10 | Vein | Once a week for 4 |
| 4 | 8 | Everolimus | 5 | 10 | Oral | Once a day for 28 days |
| 5 | 8 | Compound I | 0.1 | 10 | Oral | Once a day for 28 days |
| 6 | 8 | Compound I | 0.2 | 10 | Oral | Once a day for 28 days |
| 7 | 8 | Compound I | 0.4 | 10 | Oral | Once a day for 28 days |
| 8 | 8 | Compound I | 0.6 | 10 | Oral | Once a day for 28 days |

Note:
the solvent was 1% methylcellulose, the percentages were volume percentages.

(3) In Vivo Efficacy Results: As Shown in FIG. 1 and Table 6

TABLE 6

Evaluation of antitumor efficacy of compound I on CO-04-0032 xenograft tumor model (Based on data at day 28 after administration)

| Group | Tumor volume ($mm^3$)[a] (Day 28) | T/C[b] (%) | TGI[b] (%) |
|---|---|---|---|
| Solvent | 1582 ± 334 | — | — |
| PF05212384 (20 mg/kg) | 971 ± 249 | 68 | 44 |
| Everolimus (5 mg/kg) | 739 ± 206 | 42 | 60 |
| Compound I (0.1 mg/kg) | 760 ± 136 | 52 | 58 |
| Compound I (0.2 mg/kg) | 686 ± 171 | 39 | 64 |
| Compound I (0.4 mg/kg) | 508 ± 116 | 30 | 76 |
| Compound I (0.6 mg/kg) | 315 ± 74 | 19 | 90 |

Note:
[a]Mean ± SEM.
[b]Tumor growth inhibition was calculated from T/C and TGI (TGI (%) = $[1 - (T_{28} - T_0)/(V_{28} - V_0)] \times 100$).

Experimental results: In vivo efficacy of compound I on human-derived colorectal cancer CO-04-0032 xenograft tumor model. After administered for 28 days, compared with the Solvent 2 group, when compound I was at the dose of 0.1 mg/kg, 0.2 mg/kg, 0.4 mg/kg and 0.6 mg/kg, the T/C were: 52%, 39%, 30% and 19%, respectively, the TGI were 58%, 64%, 76% and 90%, respectively, and the p values of the three higher dose groups compared with the control group were all less than 0.05. From these results, it could be seen that in the human-derived colorectal cancer CO-04-0032 xenograft tumor model, compound I had significant antitumor effects at doses of 0.2 mg/kg, 0.4 mg/kg and 0.6 mg/kg and showed the dose-dependency. The control drug PF05212384 was in the 20 mg/kg group (T/C=68%, TGI=44%, p=0.860). Everolimus was in the 5 mg/kg group (T/C=42%, TGI=60%, p=0.027).

Experimental conclusion: the tumor inhibitory effect of compound I at a dose of 0.6 mg/kg was significantly stronger than that of PF05212384 at a dose of 20 mg/kg (p=0.041); the tumor inhibitory effect of compound I at a dose of 0.6 mg/kg was significantly stronger than that of Everolimus at a dose of 5 mg/kg (p=0.008).

Example 3 Head and Neck Cancer Clinical Trial 1

Clinical data: Subject 1, male, 40 years old. The informed consent form was made on Apr. 30, 2020. During the baseline period, examinations such as vital signs, physical examination, ECOG physical strength score, infectious disease markers, blood routine, urine routine, coagulation function, liver function, kidney function, electrolytes, fasting blood glucose, blood lipids, 12-lead electrocardiogram were performed, wherein subject 1 was suffered from right submandibular malignant pleomorphic adenoma, and the subject's tumor carried PIK3CA mutation, and the lesion was located next to the mediastinum of the right lung. First-line chemotherapy failed, baseline diameter was 26 mm. From May 12, 2020, tablets containing compound I were single administered with the dose of 1.1 mg once a day. Where, the dose of 1.1 mg contained two tablets of compound I with a specification of 0.5 mg and one tablet of compound I with a specification of 0.1 mg. After the safety of the subject was confirmed, after one week from May 18, 2020 to Nov. 26, 2021, tablets containing compound I were administered with the dose of 1.1 mg once a day. The dose of 1.1 mg contained two tablets of compound I with a specification of 0.5 mg and one tablet of compound I with a specification of 0.1 mg. Examinations such as vital signs, physical examination, blood routine, urine routine, liver function, kidney function, electrolytes, fasting blood glucose, blood lipids, 12-lead electrocardiogram were performed and clinical significance was judged to be normal; there was no serious side effects; ECOG physical strength score showed that the ability of walk freely and engagement in light physical activities, including general housework or office work; On Jul. 6, 2020, the drug was stopped due to rash, treatment with multiple oral and topical anti rash drugs was performed. After being cured, the drug was resumed on Aug. 25, 2020. Tablets containing compound I were administered with the dose of 0.7 mg once a day. A dose of 0.7 mg contained one tablet of compound I with a specification of 0.5 mg and two tablets of compound I with a specification of 0.1 mg. Tumor assessment at the 20th month was performed on Nov. 28, 2021. C20D28 tumor diameter was 16.8 mm, compared with the baseline, the tumor volume decreased by 38%, which was judged as PR.

Example 4 Head and Neck Cancer Clinical Trial 2

Clinical data: Subject 2, female, 51 years old. The informed consent form was made on Nov. 26, 2019. During the baseline period, examinations such as vital signs, physical examination, ECOG physical strength score, infectious disease markers, blood routine, urine routine, coagulation function, liver function, kidney function, electrolytes, fasting blood glucose, blood lipids, 12-lead electrocardiogram were performed, wherein the tumor was diagnosed as head and neck cancer (maxillary sinus carcinoma). The subject carried PIK3CA mutation, and the lesion was located in the left ethmoid sinus mass (baseline diameter 30 mm), sphenoid sinus mass (baseline diameter 43 mm) and multiple nodules in sphenoid sinus. The radiotherapy and chemotherapy after postoperative, immunotherapy after recurrence were ineffective. From Dec. 3, 2019, tablets containing compound I were single administered with the dose of 0.7 mg once a day. Where, the dose of 0.7 mg contained one tablet of compound I with a specification of 0.5 mg and two tablets of compound I with a specification of 0.1 mg. After the safety of the subject was confirmed, after one week from Dec. 9, 2019, the tablets containing compound I were single administered with the dose of 0.7 mg once a day. The dose of 0.7 mg contained one tablet of compound I with a specification of 0.5 mg and two tablets of compound I with a specification of 0.1 mg. Examinations such as vital signs, physical examination, blood routine, urine routine, coagulation function, liver function, kidney function, electrolytes, fasting blood glucose, blood lipids, 12-lead electrocardiogram were performed, and clinical significance was judged to be normal; starting from Dec. 10, 2019, tablets containing 0.7 mg of compound I were administered continuously every day, and the C8D28 tumor was evaluated on Jul. 20, 2020, and the tumor shrank and PR was achieved. The sphenoid sinus mass disappeared, and the subject's pain was significantly relieved and vision was restored. Tablets containing 0.7 mg of compound I was administered daily until Dec. 6, 2021, and the 26-month tumor assessment was still PR, and the progression-free survival had exceeded 26 months.

Example 5 Head and Neck Cancer Clinical Trial 3

Clinical data: Subject 3, male, 60 years old, was found to have stage IV head and neck cancer (adenoid cystic carcinoma) in 2010 and underwent left maxillary resection for surgical resection. After recurrence in 2019, treatments such as chemotherapy therapies and anti-angiogenesis inhibitors were implemented as neoadjuvant therapies, and left maxillary extended resection was performed on Jun. 9, 2020. Multiple radiotherapy treatments were performed postoperatively, but the disease still progressed. The informed consent form was made on Dec. 9, 2020. During the baseline period, examinations such as vital signs, physical examination, ECOG physical strength score, infectious disease markers, blood routine, urine routine, coagulation function, liver function, kidney function, electrolytes, fasting blood glucose, blood lipids, 12-lead electrocardiogram were performed, the requirements for enrolling in the group were met. Previous genetic testing results showed that the PIK3CA of the subject's tumor was wild type (not mutated). Screening was carried out before enrollment on Dec. 10, 2020. The location and size of the target lesions were (1) right middle lung near the pleura, with a diameter of 13.3 mm, (2) left upper lobe nodules, with a diameter of 12.8 mm; the total diameter was 26.1 mm. From Dec. 17, 2020, the tablets containing compound I were single administered with a dose of 1.1 mg once a day. The dose of 1.1 mg contained two tablets of compound I with a specification of 0.5 mg and one tablet of compound I with a specification of 0.1 mg. After the safety of the subject was confirmed, after one week, the tablets containing compound I were administered from Dec. 24, 2020 to Feb. 18, 2021, with a dose of 1.1 mg per day, once a day. The dose of 1.1 mg contained two tablets of compound I with a specification of 0.5 mg and one tablet of compound I with a specification of 0.1 mg. Examinations such as vital signs, physical examination, blood routine, urine routine, liver function, kidney function, electrolytes, fasting blood glucose, blood lipids, 12-lead electrocardiogram were performed every week (within the first month after taking the drug) or every two weeks (after the first month after taking the medicine). There was no serious side effects; ECOG physical strength score showed that the ability of walk freely and engagement in light physical activities, including general housework or office work; on Feb. 18, 2021, imaging tumor evaluation showed that the location and size of the target lesions are (1) the right middle lung near the pleura, with a diameter of 8.5 mm, (2) left upper lobe nodules, with a diameter of 12 mm and a total diameter of 20.5 mm. Compared with the baseline, the tumor volume decreased by 21.5%.

Example 6 Gastric Cancer Clinical Trial

Clinical data: Subject 4, male, 53 years old. The informed consent form was made on Nov. 5, 2019. During the baseline period, examinations such as vital signs, physical examination, ECOG physical strength score, infectious disease markers, blood routine, urine routine, coagulation function, liver function, kidney function, electrolytes, fasting blood glucose, blood lipids, 12-lead electrocardiogram were performed. The tumor was diagnosed as stage IV gastric cancer. The lesions were located in the right lobe of the liver and the right lobe of the posterior liver, and the baseline diameters were 36.4 mm and 33.1 mm. Two surgical regimens, five therapeutic regimens including chemotherapy, anti-angiogenesis inhibitors combined with chemotherapy, and immunotherapy regimens were drug-resistant for subject 4 before medication administration; from Nov. 14, 2019, tablets containing compound I were single administered with a dose of 0.7 mg once a day. The dose of 0.7 mg contained one tablet of compound I with a specification of 0.5 mg and two tablets of compound I with a specification of 0.1 mg. After the subject's safety was confirmed, one week later, from Nov. 20, 2019, the tablets containing 0.7 mg of compound I were single administered, once a day, and the dose of 0.7 mg contained one tablet of compound I with a specification of 0.5 mg and two tablets of compound I with a specification of 0.1 mg. After the first cycle, the dose was reduced to 0.4 mg, single administration, once a day, until Apr. 9, 2020 and the 0.4 mg dose contained four tablets of compound I of 0.1 mg. During the period, examinations such as vital signs, physical examination, blood routine, urine routine, coagulation function, liver function, kidney function, electrolytes, fasting blood glucose, blood lipids, 12-lead electrocardiogram were performed. Except for one time of hyperglycemia above grade 3, there were no other serious side effects; after treatment at the second month visit (C2D28), the target lesion tumor shrunk (−9%), the tumor assessment was SD (compared with the baseline tumor volume >−30% but <20%), and the progression-free survival was 5 months.

Example 7 Nasopharyngeal Carcinoma of Phase IV Clinical Trial

Clinical data: Subject 5, male, 50 years old. The informed consent form was made on Aug. 19, 2019. During the baseline period, examinations such as vital signs, physical examination, ECOG physical strength score, infectious disease markers, blood routine, urine routine, coagulation function, liver function, kidney function, electrolytes, fasting blood glucose, blood lipids, 12-lead electrocardiogram were performed. The tumor was diagnosed as stage IV nasopharyngeal carcinoma, the lesion was located in the left posterior nasopharynx, and the baseline diameter was 23.1 mm. Two surgical regimens, two radiotherapy regimens, nine different chemotherapy regimens and immunotherapy regimens before medication were all drug-resistant for subject 5 before medication administration; from Aug. 28, 2019, tablets containing compound I were single administered with a dose of 0.4 mg once a day. The dose of 0.4 mg contained four tablets of compound I with a specification of 0.1 mg. After the subject's safety was confirmed, one week later, from Sep. 3, 2019, the tablets containing compound I were single administered continuously with a dose of 0.4 mg once a day, and the dose of 0.4 mg contained four tablets of compound I with a specification of 0.1 mg. During the period, examinations such as vital signs, physical examination, blood routine, urine routine, coagulation function, liver function, kidney function, electrolytes, fasting blood glucose, blood lipids, 12-lead electrocardiogram were performed. There were no serious side effects; target lesion tumor assessment were performed every two months. The results were all SD (compared with baseline tumor volume >−30% but <20%); progression-free survival (PFS) was 10 months.

What is claimed is:

1. A method for treating or preventing cancers in digestive tract system, comprising administering to a patient a therapeutically effective amount of compound I or a pharmaceutically acceptable salt thereof, wherein the structure formula of the compound I is as follows:

I

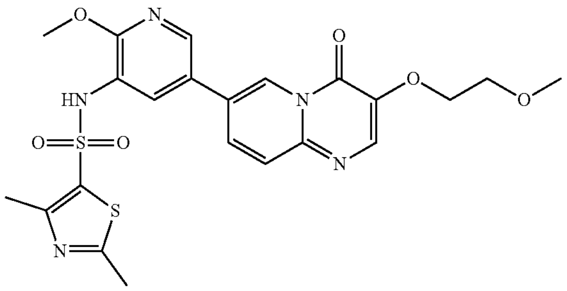

, wherein the cancer in the digestive tract system is head and neck cancer or colorectal cancer.

2. The method according to claim 1, wherein the cancer in the digestive tract system is wild-type or PIK3CA-mutated cancer in the digestive tract system.

3. The method according to claim 1, wherein the cancer in the digestive tract system is head and neck cancer.

4. The method according to claim 3, wherein the head and neck cancer is PIK3CA wild-type head and neck cancer or PIK3CA-mutated head and neck cancer.

5. The method according to claim 3, wherein the head and neck cancer is pleomorphic adenoma.

6. The method according to claim 3, wherein the head and neck cancer is maxillary sinus carcinoma or adenoid cystic carcinoma.

7. The method according to claim 1, wherein the cancer in the digestive tract system is colorectal cancer.

8. The method according to claim 1, wherein, the method further includes a step of detecting whether the patient carries PIK3CA gene mutation.

9. The method according to claim 5, wherein the head and neck cancer is malignant pleomorphic adenoma.

10. The method according to claim 1, wherein the administration dosage of the compound I or the pharmaceutically acceptable salt thereof is 0.1 mg per dose, 0.2 mg per dose, 0.3 mg per dose, 0.4 mg per dose, 0.5 mg per dose, 0.6 mg per dose, 0.7 mg per dose, 0.8 mg per dose, 0.9 mg per dose, 1.0 mg per dose, 1.1 mg per dose, 1.2 mg per dose, 1.3 mg per dose, 1.4 mg per dose, 1.5 mg per dose, 1.6 mg per dose, 1.7 mg per dose, 1.8 mg per dose, 1.9 mg per dose or 2.0 mg per dose.

11. The method according to claim 1, wherein the compound I or the pharmaceutically acceptable salt thereof is presented in an oral dosage form.

12. The method according to claim 1, wherein the compound I or the pharmaceutically acceptable salt thereof is presented in a tablet form.

13. The method according to claim 1, wherein the administration dosage of the compound I or the pharmaceutically acceptable salt thereof is 0.1-2.0 mg per dose.

14. The method according to claim 1, wherein the administration frequency of the compound I or the pharmaceutically acceptable salt thereof is once a day or twice a day.

* * * * *